United States Patent [19]

Fontayne

[11] Patent Number: 5,485,952
[45] Date of Patent: Jan. 23, 1996

[54] APPARATUS FOR APPLYING SURGICAL FASTENERS

[75] Inventor: Diego Fontayne, Norwalk, Conn.

[73] Assignee: United States Surgical Corporation, Norwalk, Conn.

[21] Appl. No.: 950,065

[22] Filed: Sep. 23, 1992

[51] Int. Cl.⁶ .................................................. A61B 17/072
[52] U.S. Cl. .................................. 227/178.1; 227/180.1; 227/19; 227/111
[58] Field of Search ........................... 227/19, 175, 176, 227/177, 178, 179, 180, 111; 606/139, 142, 143, 219, 215

[56] References Cited

U.S. PATENT DOCUMENTS

| | | |
|---|---|---|
| Re. 28,932 | 8/1976 | Noiles et al. . |
| 3,079,606 | 5/1963 | Bobrov et al. . |
| 3,490,675 | 1/1970 | Green et al. . |
| 3,499,591 | 3/1970 | Green . |
| 3,593,903 | 7/1971 | Astafiev et al. . |
| 3,675,688 | 7/1972 | Bryan et al. . |
| 3,735,762 | 5/1973 | Bryan et al. . |
| 3,819,100 | 6/1974 | Noiles et al. . |
| 3,949,924 | 4/1976 | Green . |
| 4,064,881 | 12/1977 | Meredith . |
| 4,086,926 | 5/1978 | Green et al. . |
| 4,111,206 | 9/1978 | Vishnevsky et al. . |
| 4,169,476 | 10/1979 | Hiltebrandt . |
| 4,273,129 | 6/1981 | Boebel . |
| 4,325,377 | 4/1982 | Boebel . |
| 4,383,634 | 5/1983 | Green . |
| 4,429,695 | 2/1984 | Green . |
| 4,520,817 | 6/1985 | Green . |
| 4,566,620 | 1/1986 | Green et al. ........................... 227/19 |
| 4,573,468 | 3/1986 | Conta et al. . |
| 4,573,622 | 3/1986 | Green et al. . |
| 4,580,712 | 4/1986 | Green . |
| 4,606,343 | 8/1986 | Conta et al. . |
| 4,610,383 | 9/1986 | Rothfuss et al. . |
| 4,633,874 | 1/1987 | Chow et al. . |
| 4,714,187 | 12/1987 | Green . |
| 4,715,520 | 12/1987 | Roehr, Jr. et al. . |
| 4,728,020 | 3/1988 | Green et al. . |
| 4,763,669 | 8/1988 | Jaeger ........................................ 30/251 |
| 4,784,137 | 11/1988 | Kulik et al. . |

(List continued on next page.)

FOREIGN PATENT DOCUMENTS

| | | |
|---|---|---|
| 0369324 | 5/1990 | European Pat. Off. . |
| 0505138 | 9/1992 | European Pat. Off. . |
| 2330182 | 1/1975 | Germany . |
| 51-149985 | 5/1975 | Japan . |
| 728848 | 5/1977 | U.S.S.R. . |
| 1352554 | 5/1974 | United Kingdom . |
| 1452185 | 10/1976 | United Kingdom . |
| 2048685 | 12/1980 | United Kingdom . |
| 2165559 | 4/1986 | United Kingdom . |

OTHER PUBLICATIONS

Swain et al., "An Endoscopic Sewing Machine", Gastrointestinal Endoscopy, vol. 32, No. 1, 1986.

Swain, C. P., Brown, G. J. and Mills, T. N., "An Endoscopic Stapling Device: The Development of a New Flexible Endoscopically Controlled Device for Placing Multiple Transmural Staples in Gastrointestinal Tissue", *Gastrointestinal Endoscopy*, 1989, vol. 35, No. 4, pp. 338–339.

*Primary Examiner*—Rinaldi I. Rada

[57] ABSTRACT

Surgical apparatus is provided for placing lateral lines of surgical fasteners into body tissue. The apparatus includes an endoscopic body having an elongated proximal portion and an articulating distal portion which moves relative to the proximal portion. A cartridge assembly and an anvil member are detachably mounted adjacent the articulating distal portion which move relative to one another between an open position and a closed position. A camming mechanism is associated with the articulating portion of the apparatus for moving the anvil member relative to the cartridge assembly, and a linkage system is provided for effectuating the articulation of the distal portion of the endoscopic body to increase the range of operability of the apparatus. In addition, a driving mechanism is provided for ejecting the surgical fasteners from the cartridge assembly.

30 Claims, 11 Drawing Sheets

U.S. PATENT DOCUMENTS

| | | |
|---|---|---|
| 4,819,853 | 4/1989 | Green . |
| 4,821,942 | 4/1989 | Richards et al. . |
| 4,841,888 | 6/1989 | Mills et al. . |
| 4,848,637 | 7/1989 | Pruitt . |
| 4,858,608 | 8/1989 | McQuilkin . |
| 4,869,414 | 9/1989 | Green et al. ............................. 227/19 |
| 4,880,015 | 11/1989 | Nierman . |
| 4,941,623 | 7/1990 | Pruitt . |
| 4,944,443 | 7/1990 | Oddsen et al. . |
| 4,964,559 | 10/1990 | Deniega et al. ........................ 227/178 |
| 4,978,049 | 12/1990 | Green . |
| 5,040,715 | 8/1991 | Green et al. . |
| 5,042,707 | 8/1991 | Taheri ................................. 227/179 X |
| 5,071,430 | 12/1991 | de Salis et al. . |
| 5,099,827 | 3/1992 | Melzer et al. ....................... 606/142 X |

APPARATUS FOR APPLYING SURGICAL FASTENERS

BACKGROUND OF THE INVENTION

1. Field of the Invention

This invention relates to surgical stapling apparatus, and more particularly to surgical apparatus for performing sequential operations such as tissue clamping, staple forming and/or tissue cutting.

2. Description of Related Art

Surgical stapling apparatus is known wherein tissue is first grasped or clamped between opposing jaw structure and then fastened by means of fasteners. In some instruments a knife is provided to cut tissue which has been joined. The fasteners are typically in the form of surgical staples however, two part polymeric type fasteners are also known.

Instruments for this purpose can comprise two elongated members which are respectively used to capture or clamp tissue. Typically, one of the members carries a disposable cartridge housing wherein a plurality of staples are arranged in at least two lateral rows while the other member defines an anvil for forming the staple legs into a hook-like configuration as they are driven against the anvil. The stapling operation is effected by a pusher which travels longitudinally along the cartridge carrying member, acting upon the staples so as to place them in lateral rows in the body tissue. A knife may be optionally positioned in such a manner so as to operate immediately behind the pusher, and laterally positioned between the staple rows to longitudinally cut and/or open the stapled tissue between the rows of staples. Such instruments are disclosed for example in Bobrov et al. (U.S. Pat. No. 3,079,606) and Green (U.S. Pat. No. 3,490,675). These instruments comprise apparatus for simultaneously making a longitudinal incision and applying a row of staples on both sides of the incision.

A later development disclosed in Green (U.S. Pat. No. 3,499,591) applies a double row of staples on each side of the incision. This is accomplished by a cartridge assembly having a cam member which moves within a guide path between two sets of staggered staple carrying grooves. Staple drive members are located within the grooves for being contacted by the longitudinally moving cam member as it is driven along the groove to effect ejection of the staples.

The instruments described above were all designed to be used in surgical procedures in which surgeons have direct manual access to the operation site. However, in endoscopic or laparoscopic procedures surgery is performed from a location remote from the operative site through a small incision or through narrow cannulae inserted through small entrance wounds in the skin. In order to address the specific needs of endoscopic and/or laparoscopic surgical procedures, an endoscopic surgical stapling apparatus such as that which is shown in Green et at. (U.S. Pat. No. 5,040,715) has been developed. This apparatus is well suited for such procedures and incorporates a distal end having an anvil and staple cartridge assembly and a manually operated handle assembly interconnected by an endoscopic portion which permits the instrument to be inserted into a cannula and be remotely operated by the surgeon.

Many of the instruments described above are limited in their range of operability. Improvements have been made in the art of surgical instruments to increase their range of operability. For example, Nierman (U.S. Pat. No. 4,880,015) discloses a biopsy forceps designed for use through a flexible fiberoptic bronchoscope. The biopsy forceps includes a handle connected to a thin elongated flexible shaft with a distal portion thereof hinged to the shaft. A grasping tool or biopsy forceps is attached to the distal hinged portion. Control wires extend from the handle through the distal portion to the shaft for controlling the angular rotation of the distal portion of the instrument to increase its range of operability.

In accordance with these and other principles, it is an object of the present invention to provide a surgical apparatus for driving surgical fasteners into body tissue which apparatus may be operated from a location remote from the surgical site.

It is another object of the present invention to provide a surgical apparatus insertable through a small incision or narrow tube for driving surgical fasteners into body tissue and cutting the body tissue between the rows of staples.

It is another object of the present invention to provide a surgical apparatus for driving surgical fasteners into body tissue which apparatus has an increased range of operability.

It is still another object of the present invention to provide a surgical apparatus having sealing structure for inhibiting the escape of insufflation gas through the apparatus.

Yet another object of the present invention to provide a surgical apparatus for driving staples which is adapted for mounting a replaceable cartridge assembly.

SUMMARY OF THE INVENTION

The surgical instrument in accordance with an embodiment of the present invention is a surgical stapling apparatus adapted for placing one or more longitudinal rows of staples in body tissue. This apparatus may include a knife for making an incision in the body tissue between the rows of staples. The latter configuration may find particular use in joining two hollow organs or in removing an organ, such as the appendix or gallbladder.

In a preferred embodiment of the subject invention, the endoscopic stapler comprises a tubular body having an elongated proximal portion and an articulating distal portion adapted for detachably mounting a cartridge assembly. A linkage mechanism is associated with the tubular body of the instrument for effectuating the articulation of the distal portion of the tubular body relative to the proximal portion thereof and includes a pair of elongated rod members extending through the endoscopic body and actuated from a location remote from the distal end portion of the apparatus. The cartridge assembly comprise a cartridge housing for supporting a cartridge which contains a plurality of surgical staples slidably mounted therein, and has a tissue engaging surface formed thereon. An anvil member is mounted adjacent the cartridge housing and is provided with a staple forming surface against which staples ejected from the cartridge are driven. The anvil member is movable between an open position and a closed position wherein the staple forming surface is in close cooperative alignment with the tissue engaging surface of the cartridge.

The apparatus includes camming means which are associated with the cartridge assembly for moving the anvil member between the open position and the closed position. The camming means comprises a cam tube having a camming surface disposed around at least a portion of the anvil member and movable between a first position wherein the camming surface is located proximal to a camming portion of the anvil member, corresponding to the anvil member being open, and a second position wherein the camming surface is located distal to the camming portion of the anvil member, corresponding to the anvil member being closed.

The apparatus further includes means for ejecting the surgical staples from the cartridge in such a manner so as to cause the staples to form against the staple forming surface of the anvil member. The means for ejecting the surgical fasteners comprises a plurality of pusher elements in abutment with the surgical fasteners, and a cam plate for actuating the pusher elements. The cam plate is mounted for translation within the cartridge assembly and is operatively connected to a plunger member extending through the tubular body of the apparatus and actuated from a location remote from the cartridge assembly.

The surgical apparatus of the subject invention further comprises sealing means associated with the tubular body portion of the instrument for inhibiting the egress of insufflation gas therethrough during surgical procedures. Preferably, the sealing means includes a first annular seal member disposed adjacent the proximal end of the tubular body and a second annular seal member disposed at the distal end of the tubular body adjacent the articulating portion thereof.

Further features of the invention, its nature, and various advantages will become more apparent from the accompanying drawing and the following detailed description of the invention.

BRIEF DESCRIPTION OF THE DRAWINGS

Preferred embodiments of the subject invention will be described hereinbelow with reference to the drawings wherein:

FIGS. 12–14 are side elevational views, partially broken away, of the cartridge assembly of the apparatus of FIG. 1 during a staple driving sequence wherein:

DETAILED DESCRIPTION OF THE PREFERRED EMBODIMENTS

Because endoscopic procedures are more common than laparoscopic procedures, the present invention shall be discussed in terms of endoscopic procedures and apparatus. However, use herein of terms such as "endoscopic," "endoscopically" and "endoscopic portion", among others, should not be construed to limit the present invention to a stapling and cutting apparatus for use only in conjunction with an endoscopic tube. To the contrary, it is believed that the present invention may find use in procedures where access is limited to a small incision including but not limited to laparoscopic procedures. Also, as used herein the terms "fasteners" and "staples" shall be treated equivalently. Unless otherwise stated, the term "cartridge assembly" shall include at least the cartridge itself and staples or fasteners and staple drive members disclosed therein.

In the drawings and the description which follows, the term "proximal" refers to the end of the apparatus which is closest to the operator, while the term "distal" will refer to the end which is furthest from the operator.

Figure 1:
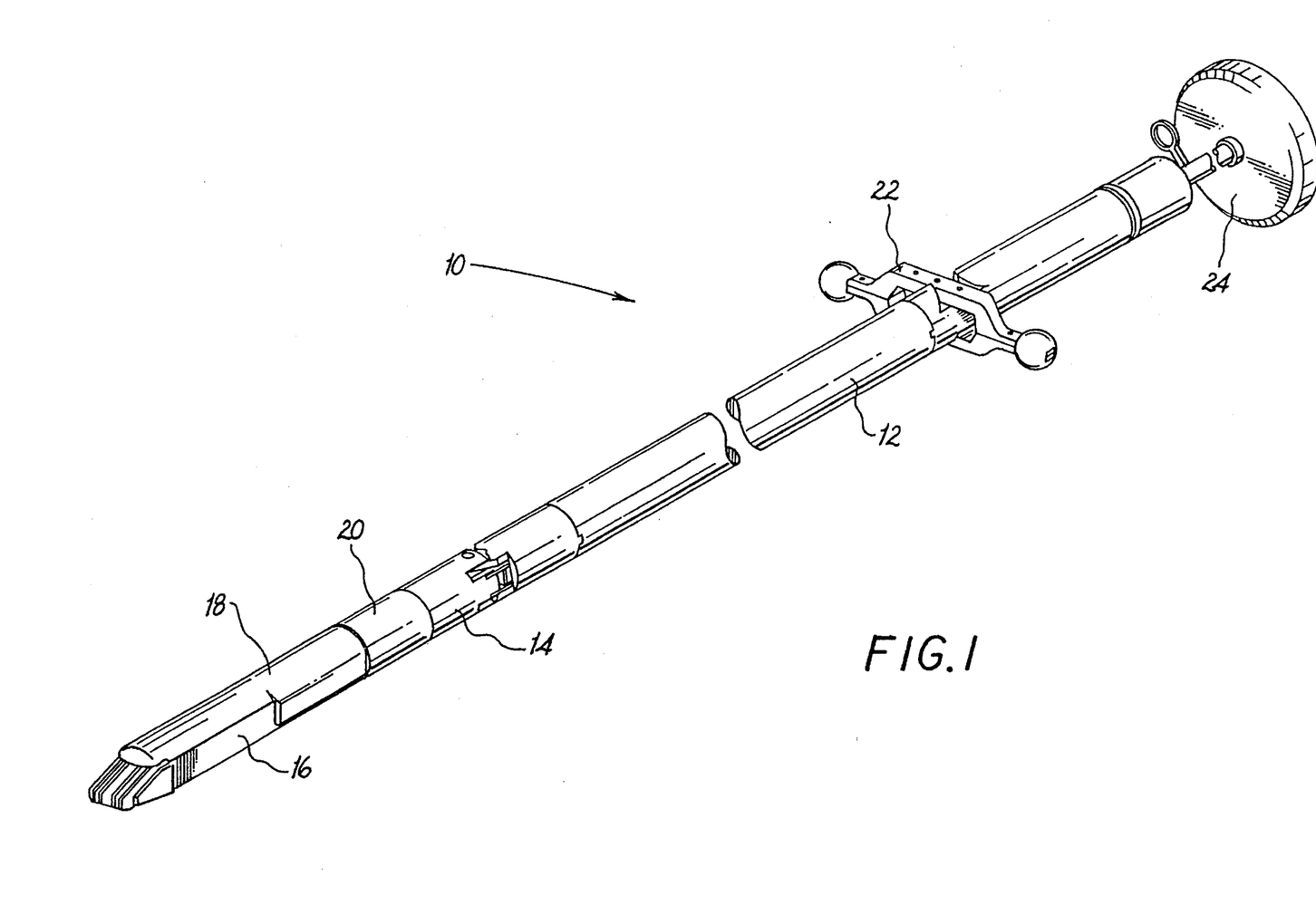
FIG. 1 is a perspective view of an apparatus for driving surgical fasteners in accordance with a preferred embodiment of the subject invention.

A surgical stapling apparatus in accordance with a preferred embodiment of the subject invention is illustrated in FIG. 1 and is designated generally by reference numeral 10. Surgical apparatus 10 comprises a tubular endoscopic body including an elongated proximal portion 12, and an articulating distal portion 14 which is mounted for movement relative to the longitudinal axis of proximal portion 12. A cartridge assembly is detachably mounted adjacent the distal end of articulating portion 14 which includes a cartridge housing 16 containing a plurality of surgical fasteners and an anvil member 18 against which the surgical fasteners are driven as they are ejected from the cartridge assembly. Anvil member 18 is movable relative to cartridge housing 16 between a normally open position and a closed position by means of a camming mechanism which includes a cam tube assembly 20 associated with the articulating portion 14 of proximal portion 12 and configured for actuation by means of a reciprocating plunger assembly which extends longitudinally through proximal portion 12 from a location remote from the surgical site.

The movement of the articulating portion 14 of surgical apparatus 10 is effectuated by a linkage assembly which is disposed within the proximal portion 12 and which is operated through remote manipulation of a pivoting handle 22 which is operatively connected to the linkage assembly. Once the distal portion 14 of the apparatus 10 has been articulated to a desired position, and body tissue has been engaged between the anvil member 18 and the cartridge housing 16, surgical apparatus 10 may be fired so as to drive a plurality of surgical fasteners from the cartridge assembly by remote operation of a plunger assembly 24 which extends longitudinally through the proximal portion 12 of surgical apparatus 10.

Figure 2:
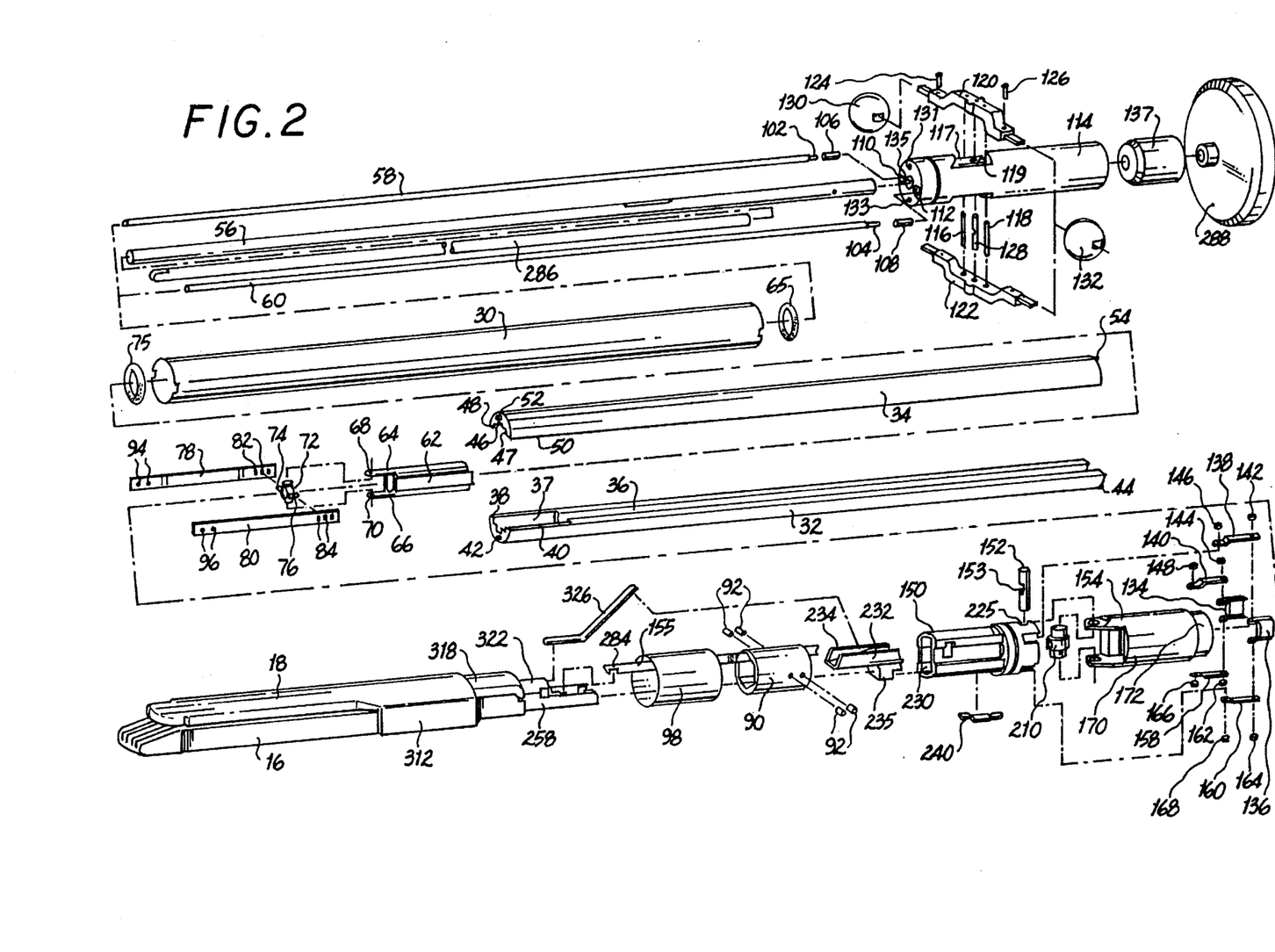
FIG. 2 is an exploded perspective view of the surgical apparatus of FIG. 1.

Referring to FIG. 2, the proximal portion 12 of surgical apparatus 10 includes an elongated support tube 30 which houses a pair of elongated tube inserts 32 and 34. Tube insert 32 is provided with a longitudinal central channel 36 the distal end portion 37 of which has a diameter which is slightly larger than the remainder thereof, and opposed lateral grooves 38 and 40 formed on either side of central channel 36. Opposed anchor pins 42 and 44 extend from the opposed proximal and distal ends of tube insert 32, respectively, for anchoring tube insert 32 within the proximal portion 12 of apparatus 10. Tube insert 34 has structure corresponding to that of tube insert 32 including a longitudinal central channel 46 having an enlarged distal end portion 47, opposed lateral grooves 48 and 50, and anchor pins 52 and 54. When tube inserts 32 and 34 are arranged within support tube 30, central channels 36 and 46 define an elongated central passageway for a clamp rod 56, and lateral grooves 38 and 48, and 40 and 50 respectively define lateral passageways for articulator rods 58 and 60 which interconnect with the linkage mechanism for moving the articulating portion 14 of relative to the proximal portion 12 thereof. A pair of annular sealing members 65 and 75 are provided in proximal portion 12 for inhibiting the egress of insufflation gas therethrough. In particular, sealing member 65 is disposed adjacent the proximal end of proximal portion 16 while sealing member 75 is disposed in the distal end of proximal portion 16 adjacent proximal pivot member 154.

Figure 6:
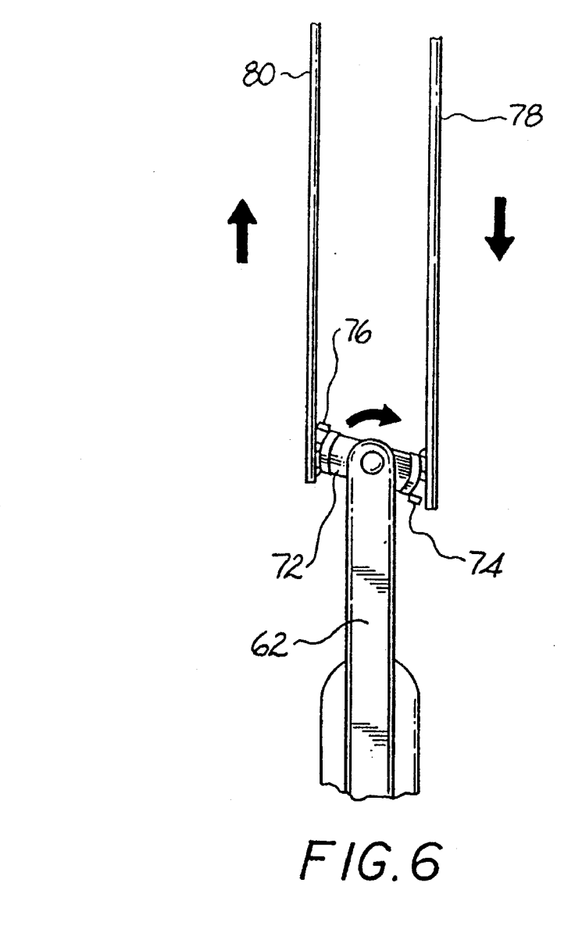
FIG. 6 is a top plan view of a linkage of the apparatus of FIG. 1, illustrating the relative movement of the members thereof.
Figure 9:
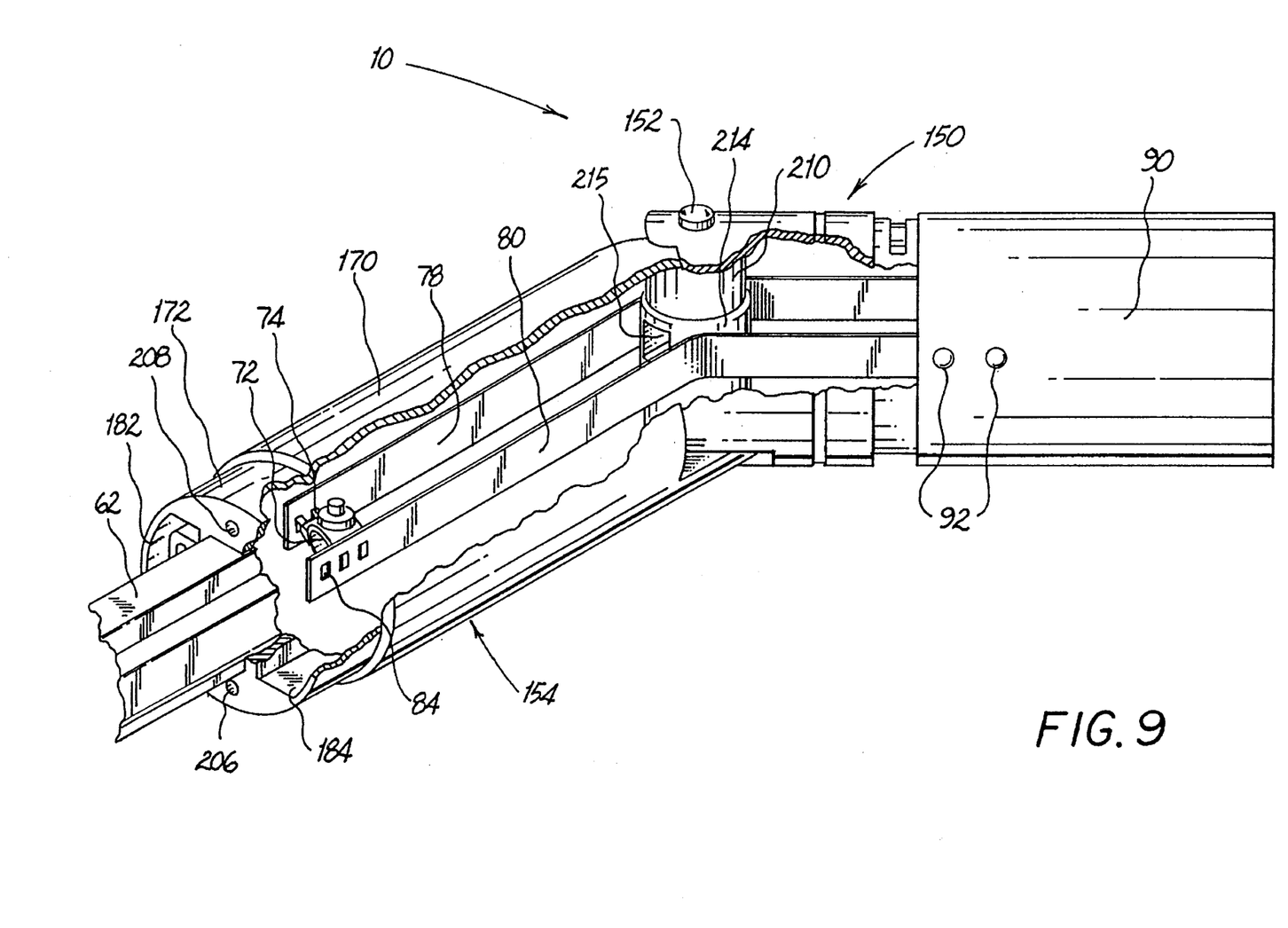
FIG. 9 is an enlarged perspective view of the articulating portion of the apparatus of FIG. 1.

A clamp yoke 62 is mounted rigidly at the distal end of clamp rod 56 and is dimensioned for being maintained within the distal end portions 37 and 47 of the central passageway defined by channels 36 and 46. Clamp yoke 62 is formed with a pair of opposed flange portions 64 and 66 each having an aperture 68 and 70, respectively, for mounting a pivoting gear 72 which is adapted to pivot about an axis which is perpendicular to the longitudinal axis of the elongated clamp rod 56. Diametrically opposed toothed portions 74 and 76 are formed on the circumference of gear 72 for operatively meshing with a pair of flexible links 78 and 80. In particular, the proximal end portion of link 78 is provided with a plurality of spaced apart apertures 82 for meshing with toothed portion 74 on gear 72, and link 80 is similarly provided at the proximal end thereof with a plurality of spaced apart apertures 84 for operatively meshing with the toothed portion 76 of gear 72. As best seen in FIGS. 6 and 9, pivotal movement of gear 72 about the perpendicular axis thereof will cause corresponding longitudinal translation of links 78 and 80 in opposed longitudinal directions. The flexible links 78 and 80 may be formed from stainless steel or a similar material. Preferably, however, the flexible links 78 and 80 are formed from a shape memory alloy comprising nickel and titanium such as that which is disclosed in U.S. Pat. No. 4,665,906 to Jervis. In doing so, the links 78 and 80 will not acquire an undesirable set when the distal portion 14 of surgical apparatus 10 is articulated.

The distal end portions of links 78 and 80 are associated with cam tube assembly 20 and, in particular, are respectively connected to a collar tube 90 by a plurality of collar pins 92 which extend through apertures 94 in the distal end portion of collar link 78 and apertures 96 in the distal end portion of link 80 for being received in mounting ports 95 in collar tube 90. Collar tube 90 is disposed within a cover tube 98 and functions as a cam member for operatively moving anvil member 18 between a normally open position and a closed position relative to cartridge housing 16.

As discussed hereinabove, the articulation of the distal end portion 14 relative to the proximal portion 12 is effectuating by means of a linkage mechanism which includes articulator rods 58 and 60. The proximal end portions of articulator rods 58 and 60 are respectively provided with pin portions 102 and 104 for receiving rod adapters 106 and 108, respectively. Rod adapters 106 and 108 extend through a pair of corresponding longitudinal bore holes 110 and 112 which are provided in an elongated cylindrical handle support 114. Rod adapters 106 and 108 operatively contact respective transverse rod pins 116 and 118 which extend through slots 117 and 119 to associate with an articulator link assembly which includes a pair of generally U-shaped articulator links 120 and 122. Articular links 120 and 122 are connected to one another by link pins 124 and 126 and is pivotable about a transverse axis or a cylindrical support pin 128. Opposed spherical articulator handles 130 and 132 are mounted to articulator links 120 and 122. In addition, a pair of opposed apertures 131 and 133 are defined in support handle 114 for receiving anchor pins 44 and 54, respectively. A center bore 135 extends through handle support 114 for receiving collar rod 56. A handle clamp 137 is also provided for mounting at the proximal end of collar rod 56. Rotation of the articulator link assembly about pivot pin 128 will cause corresponding longitudinal movement of articulator rods 58 and 60 in opposed longitudinal directions with respect to the proximal portion 12.

The distal end portions of articulator rod members 58 and 60 are engaged in substantially C-shaped adapter links 134 and 136, respectively. Adapter link 134 is independently connected to upper and lower joint links 138 and 140 by adapter pins 142 and 144. Joint pins 146 and 148 connect joint links 138 and 140 to a distal joint member 150 which is pivotably connected by a transverse pivot pin 152 having a perpendicular bore 153 for receiving a flexible actuator link 155, to a proximal pivot member 154 which comprises a section of the articulating portion 14 of surgical apparatus 10. Similarly, adapter link 136 is operatively connected to a pair of upper and lower joint links 158 and 160 by adapter pins 162 and 164 and joint pins 166 and 168 operatively connect articulator link 136 to the distal joint member 150. Longitudinal translation of articular rods 58 and 60 will cause corresponding articulation of adapter links 134 and 136 causing distal joint member 150 to pivot relative to proximal pivot member 154 about transverse pivot pin 152.

Figure 3:
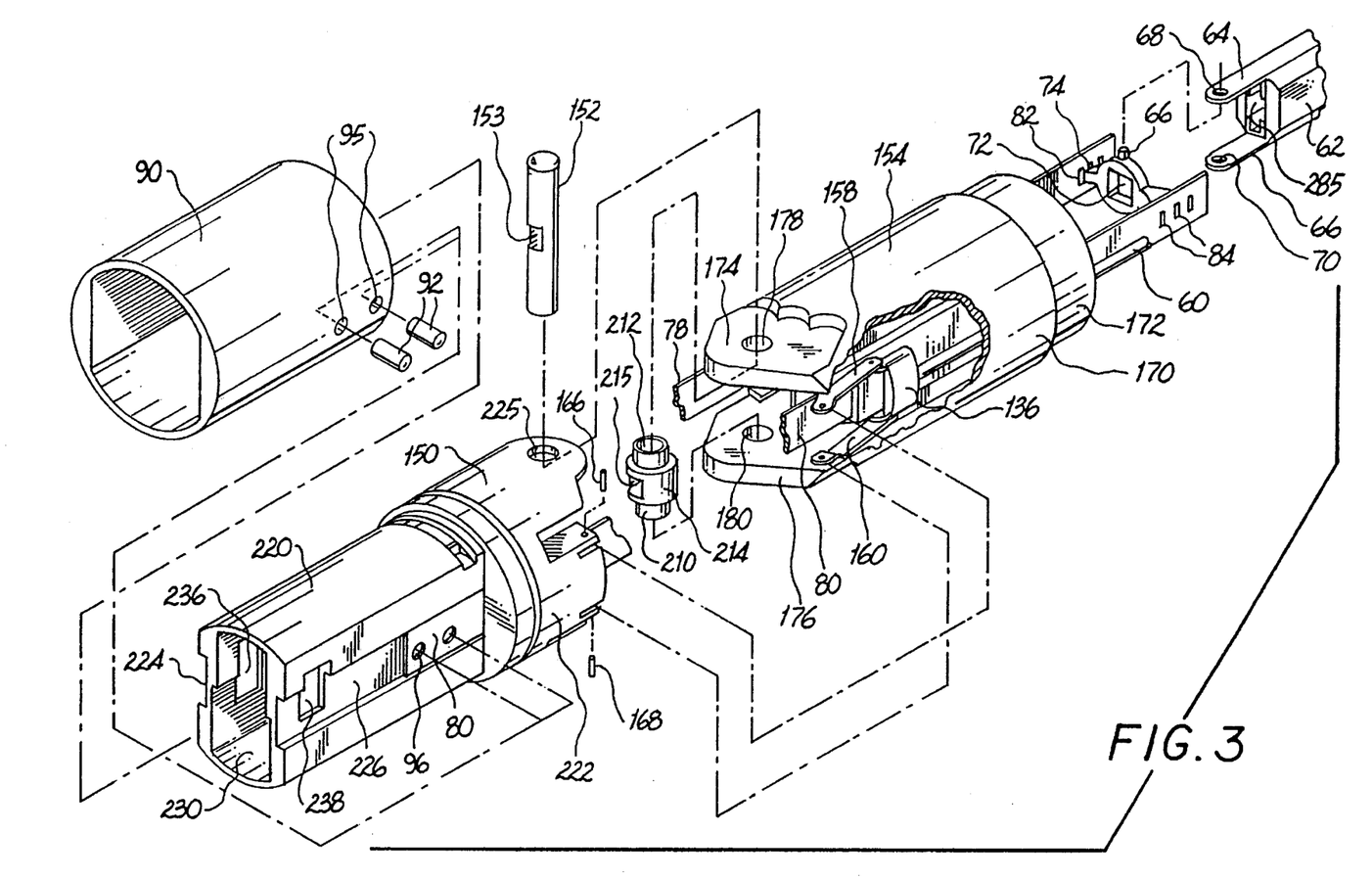
FIG. 3 is an enlarged perspective view, partially broken away, of the articulating portion of the apparatus of FIG. 1.
Figure 5:
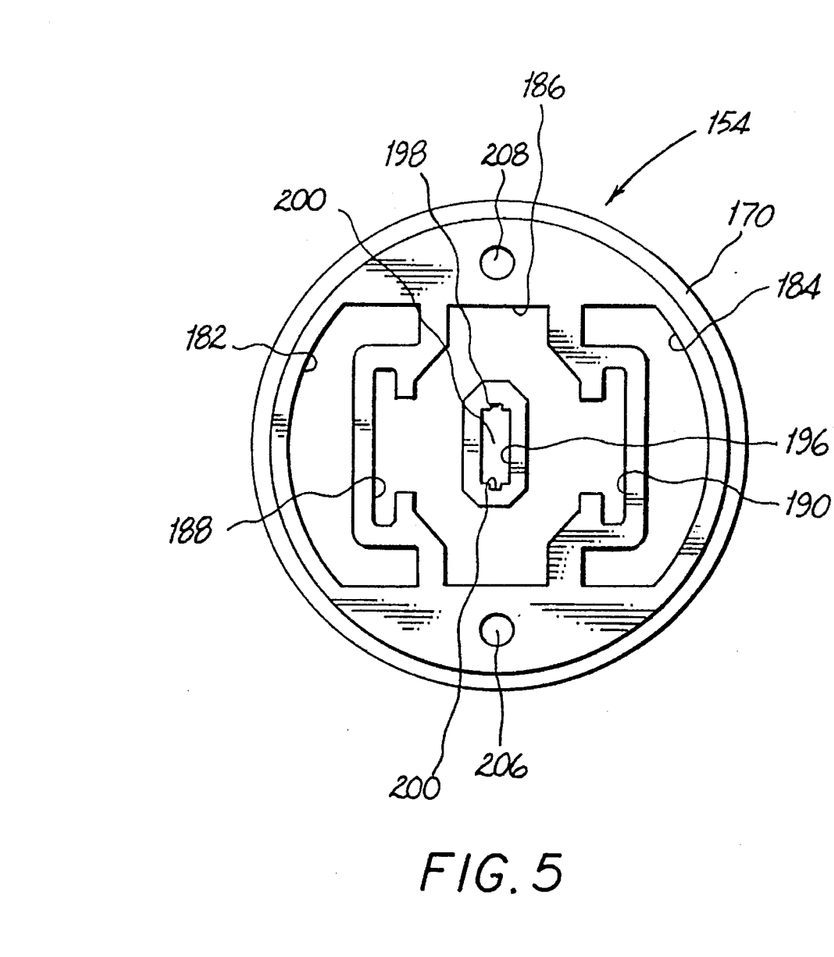
FIG. 5 is a rear elevational view of the articulating portion of the apparatus of FIG. 1, showing the internal structure defined therein.

Referring to FIG. 3, the proximal pivot member 154 which is operatively associated with the articulating portion 14 of surgical apparatus 10 comprises a generally cylindrical body portion 170 which includes a proximal engaging section 172 mountable within the distal end of support tube 30. A pair of opposed mounting flanges 174 and 176 extend distally from cylindrical body portion 170 each having an aperture 178 and 180, respectively, for receiving pivot pin 152 which joins proximal pivot member 154 to distal joint member 150. A plurality of longitudinal chambers are defined within the proximal pivot member 154 for maintaining various elements of the apparatus 10 of the subject invention. In particular, referring to FIG. 5, a pair of opposed generally C-shaped lateral chambers 182 and 184 are provided therein for maintaining the C-shaped adapter links 134 and 136, respectively. In addition, substantially rectangular channels 188 and 190 are defined in pivot member 154 adjacent C-shaped channels 182 and 184 respectively, for receiving and maintaining links 78 and 80, respectively. A rectangular channel 186 is defined in the center of proximal pivot member 154 which is dimensioned for receiving gear member 72 and permitting its rotational movement when closing anvil member 18 through translation of the cam tube assembly 20. An internal chamber 196 having a generally rectangular cross-section and defining upper and lower tracks 198 and 200 extends longitudinally through proximal pivot member 154 for supporting the flexible actuator link 155. A pair of opposed bores 206 and 208 are provided in pivot member 154 for receiving anchor pins 42 and 52, respectively.

A cylindrical yoke member 210 is also associated with the proximal pivot member 154 and the distal joint member 150.

Yoke member 210 has an elongated central bore 212 for receiving pivot pin 152, and a cylindrical barrel shaped body portion 214 which functions as a bearing surface for the flexible links 78 and 80 as they are flexed during articulation of distal end portion 14. A rectangular passageway 215 extends through body portion 214 for accommodating flexible actuator link 155.

The distal joint member 150 has a generally cylindrical body portion 220 which defines an engaging section 222 at the proximal end thereof for receiving the joint pins from joint links 138 and 140, and, in addition, for inter-engaging pivot pin 152 through aperture 225. Body portion 220 is provided with a pair of opposed lateral slots 224 and 226 within which links 78 and 80 respectively travel in a longitudinal direction in response to movement of clamp rod 56. A generally rectangular channel 230 extends longitudinally through the body portion 220 of distal joint member 154 wherein a joint insert 232 (see FIG. 2) is positioned for releasably engaging anvil member 18 and cartridge assembly 16. In particular, a lower chamber 235 of joint insert 232 is provided for receiving a mounting portion of cartridge housing member 16 and an upper chamber portion 234 of insert 232 is provided for releasably mounting a portion of anvil member 18. Furthermore, a pair of opposed generally rectangular slots 236 and 238 are provided in the walls of body portion 220 for permitting transverse movement of anvil member 18 relative to cartridge assembly 16 to effectuate the engagement of body tissue. A leaf spring member 240 (see FIG. 2) is also associated with the distal joint member 150 for cooperating with cartridge member 16.

Figure 4:
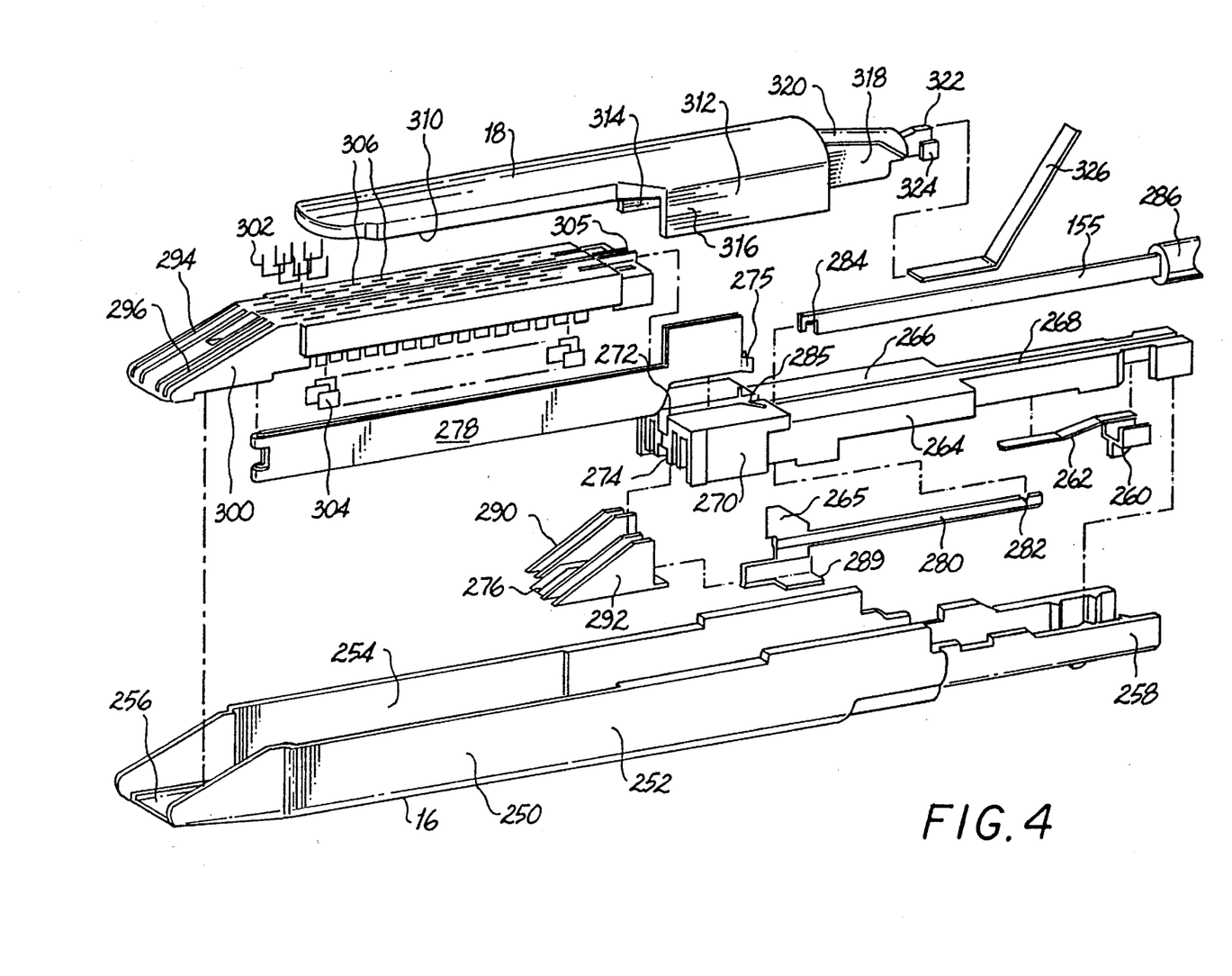
FIG. 4 is an exploded perspective view of the cartridge assembly of the apparatus of FIG. 1.

Turning to FIG. 4, cartridge housing 16 of the cartridge assembly of surgical apparatus 10 comprises a channel portion 250 defined by opposed lateral walls 252 and 254 and a bottom wall 256. A cartridge mounting portion 258 extends proximally from channel portion 250 and is engagable in the pivot insert 232 which is disposed in the rectangular channel 230 formed in distal joint member 150. A detent member 260, which is mounted on a resilient leaf spring 262, is associated with the cartridge mounting portion 258 of cartridge housing 16 for detachable engagement with the leaf spring 240 associated with the distal joint member 150. A cartridge adapter 264 is disposed within the channel portion 250 of cartridge housing 16 which includes a platform structure 266 having a longitudinal track 268 defined therein, and a slotted structure 270 having a longitudinal groove 272 formed therein. A plurality of slots 274 are provided in slotted structure 270 for receiving a cam plate 276 which is configured for ejecting staples from the cartridge assembly during stapling procedures. A support bar 278 is configured to be mounted within longitudinal groove 272 for defining a passageway within which a surgical knife member 265 travels as it traverses the cartridge housing 16 cutting tissue as staples are ejected from the cartridge assembly. In particular, winged tabs 275 are provided in the proximal portion of support bar 278 for engagement in a corresponding winged slit 285 in platform 266. Surgical knife 265 comprises an elongated shank portion 280 having a cross-section which is dimensioned and configured for travel within the internal chamber 196 of proximal pivot member 154 and the longitudinal track 268 defined in cartridge adapter 264. A V-shaped notch 282 is provided in the proximal end of shank portion 280 for engaging a hook 284 formed on the distal end of elongated flexible actuator link 155 which is attached to an actuator rod 286 extending through a tracked passageway 285 provided in collar rod 56. Actuator rod 286 is mounted to an actuator handle 288 (see FIG. 2) for remotely driving staples. Actuator link 155 is also dimensioned and configured for travel within the longitudinal track 268 of cartridge adaptor 264 and the internal chamber 196 of pivot member 154. A wing-like structure 289 is formed at the distal end of surgical knife 265 for engaging the cam plate 276.

Cam plate 276 is formed with a pair of dual plates 290 and 292 of triangular configuration which are disposed in staggered fashion for promoting more effective ejection of the staples from the cartridge assembly. The dual cam plates 290 and 292 are dimensioned for traversing corresponding dual slots 294 and 296 which are formed in a cartridge element 300 mounted within the channel portion 250 of cartridge housing 16 and containing a plurality of surgical fasteners 302. A longitudinal groove 305 is also defined in cartridge element 300 for accommodating surgical knife 265. As the dual plates 290 and 292 of cam plate 276 traverse their respective dual slots 294 and 296 and knife 265 travels within groove 305, pusher elements 304 are driven upwardly within corresponding cavities 306 defined in cartridge element 300 for ejecting the staples 02 therefrom, driving them against a staple forming surface defined on anvil member 18.

Anvil member 18 comprises a staple forming portion 310 which extends from a shroud portion 312 having opposed lateral walls 314 and 316 for mounting anvil member 18 adjacent cartridge housing 16 and an anvil mounting portion 318 having a cam surface 320 which cooperates with the collar tube 90 for camming anvil member 18 between the open and closed positions, and an engagement head 322 which includes opposed tabs 324 for engagement in opposed slots 236 and 238 in the walls of the distal joint member 150. An anvil spring 326 is associated with the anvil mounting portion 318 for biasing the anvil member 18 in an open position.

Figure 8:
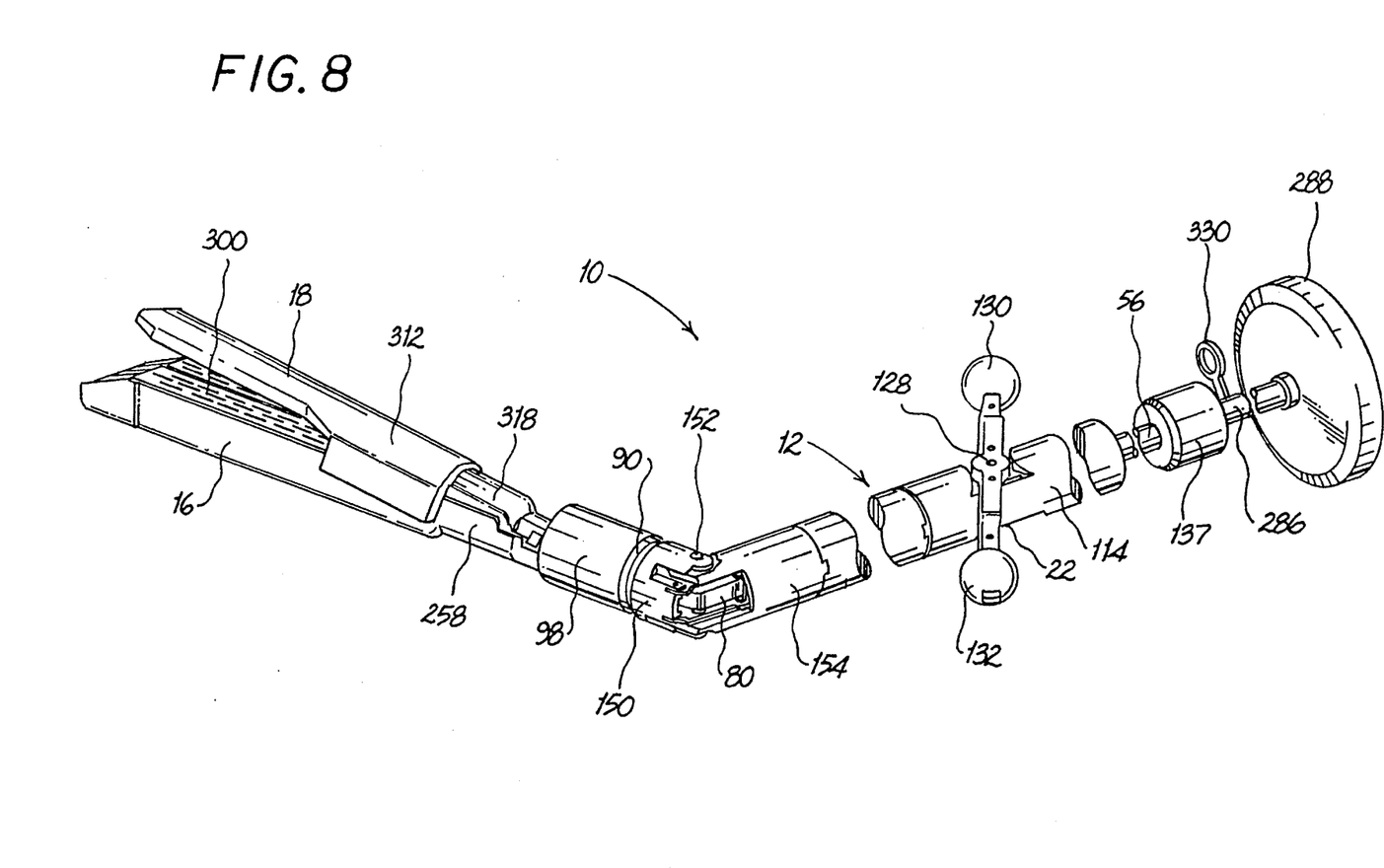
FIG. 8 is a perspective view of the surgical apparatus of FIG. 1 in an articulated condition, wherein the cartridge assembly thereof is in an open position.

Referring to FIGS. 8–11, in use the surgical apparatus 10 is introduced into the abdominal cavity of a patient through a trocar or cannula extending through a small incision or entrance wound device whereupon the camming mechanism 20 of the instrument is in its proximal most position permitting the anvil member 18 to be in an open position biased by anvil spring 326, as illustrated in FIG. 8. Thereafter, the user may articulate the distal portion 14 of surgical apparatus 10 into a desired position through remote operation of articulator links 120, 122 as shown in FIG. 9.

Figure 7:
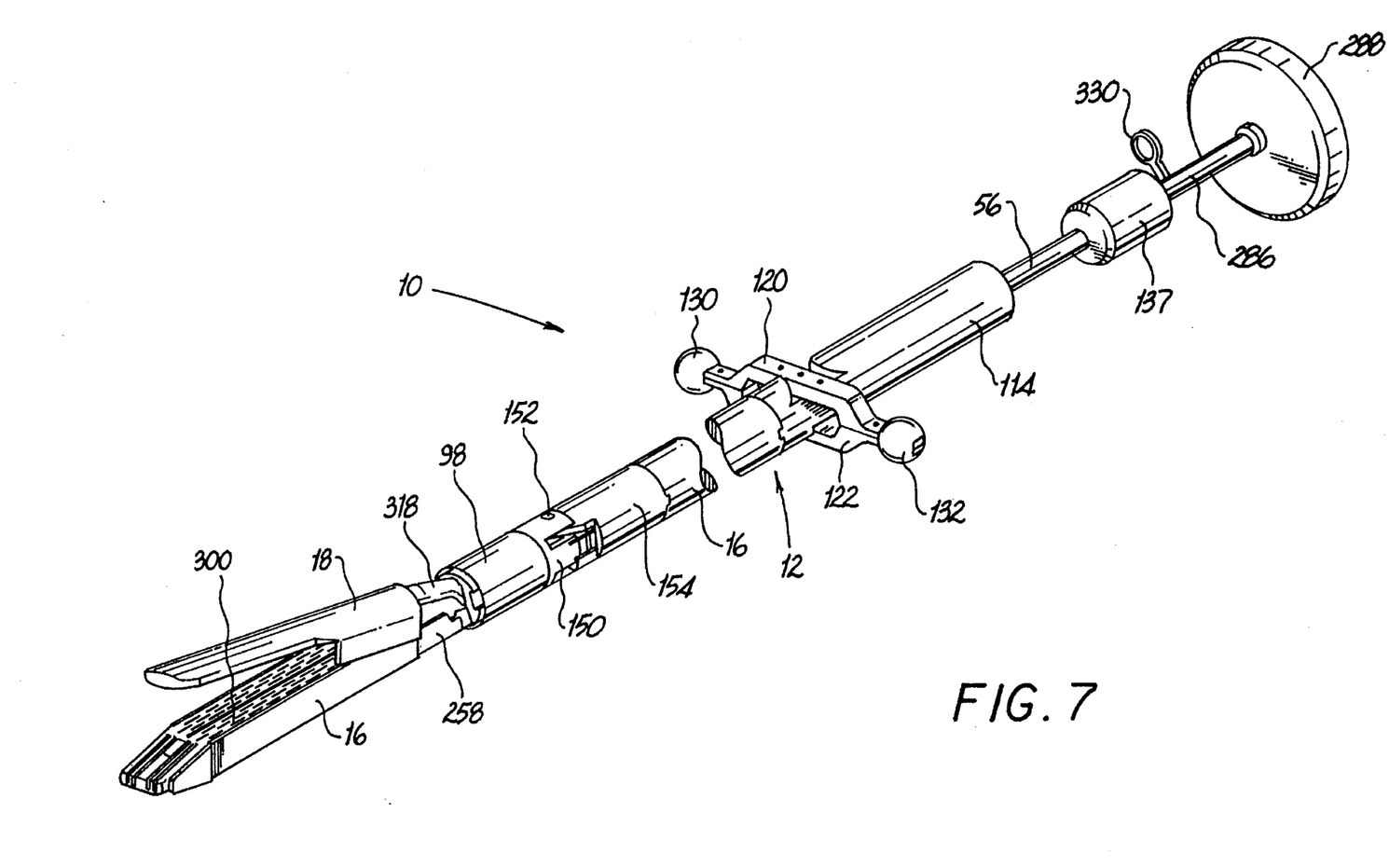
FIG. 7 is a perspective view of the surgical apparatus of FIG. 1, with the cartridge assembly thereof in an open position.
Figure 10:
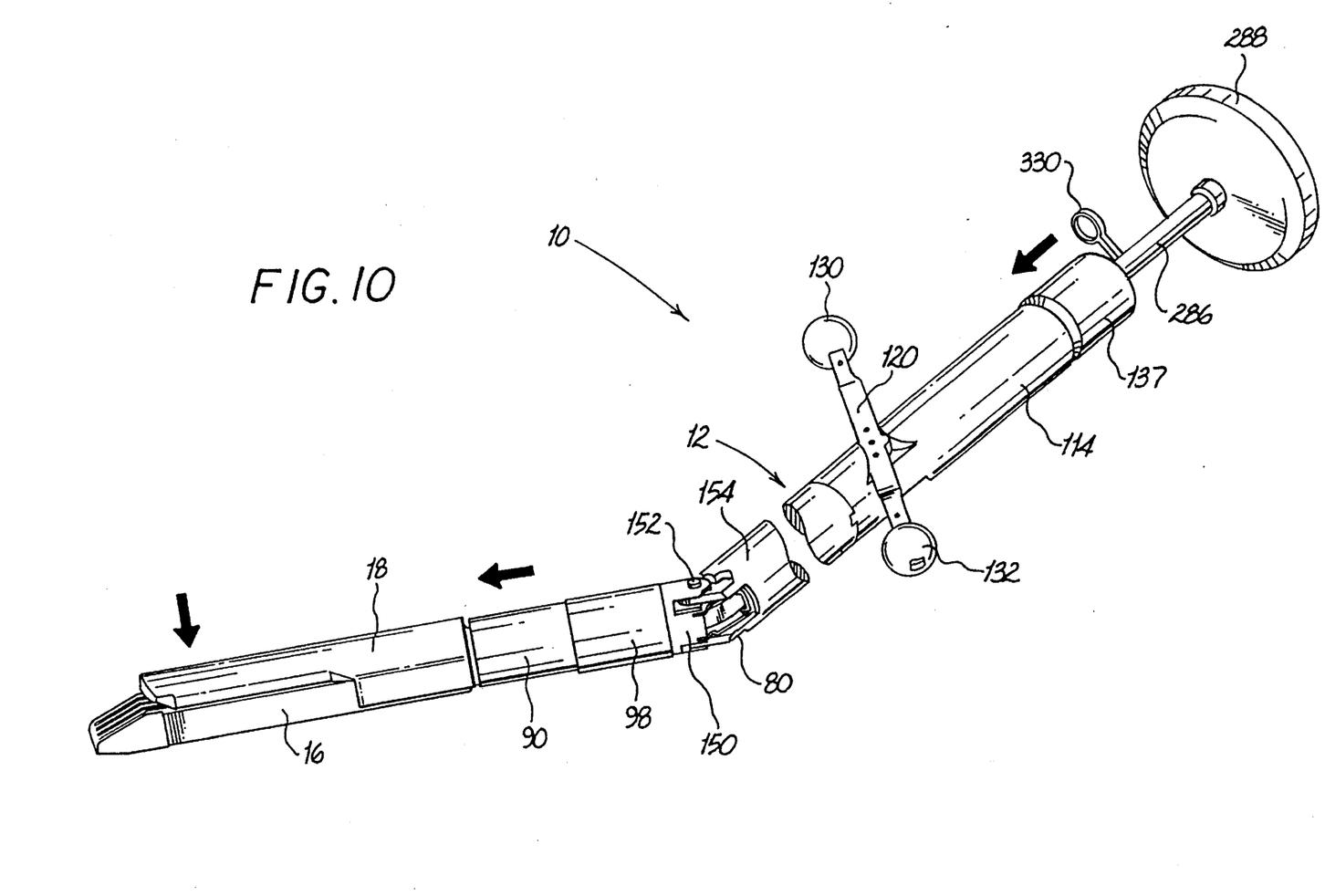
FIG. 10 is a perspective view of the surgical apparatus of FIG. 1 in an articulated condition, with the cartridge assembly thereof in a closed position.

Rotation of articulator links 120, 122 in a clockwise direction will cause corresponding clockwise movement of the distal portion 14 within a 45° sector of rotation, while rotation of articulator links 120, 122 in a counter-clockwise direction will move the distal portion 14 in a counter-clockwise direction within a 45° sector of rotation, such that the range of operability of surgical apparatus 10 is increased to function within a 90° sector of rotation. Upon rotation of the articulator links 120, 122 flexible collar links 78 and 80 will move longitudinally relative to one another (see FIG. 7) and will be flexed about the cylindrical barrel portion 214 of yoke link 210 as it acts as a bearing surface to prevent the flexible links 78 and 80 from obtaining an undesirable set as they are compressed as best seen in FIG. 10. Once the user has positioned the articulating distal portion 14 in a desired position, body tissue to be stapled and/or cut may be engaged between the cartridge housing 16 and the anvil member 18. Thereupon, the user may drive the handle clamp 137 in a distal direction, driving clamp rod 56 distally within the central passageway defined by tube inserts 32 and 34 of support tube 30. Subsequently, the flexible links 78 and 80 are driven in a generally distal direction as gear member 72 is forced forward. As flexible links 78 and 80 slide forward within lateral slots 224 and 226 in distal joint member 150, collar tube 90 is urged in a distal direction camming the anvil member 18 into a closed position as it cams against the camming surface 320 defined on the mounting portion 318 of anvil member 18.

Figure 11:
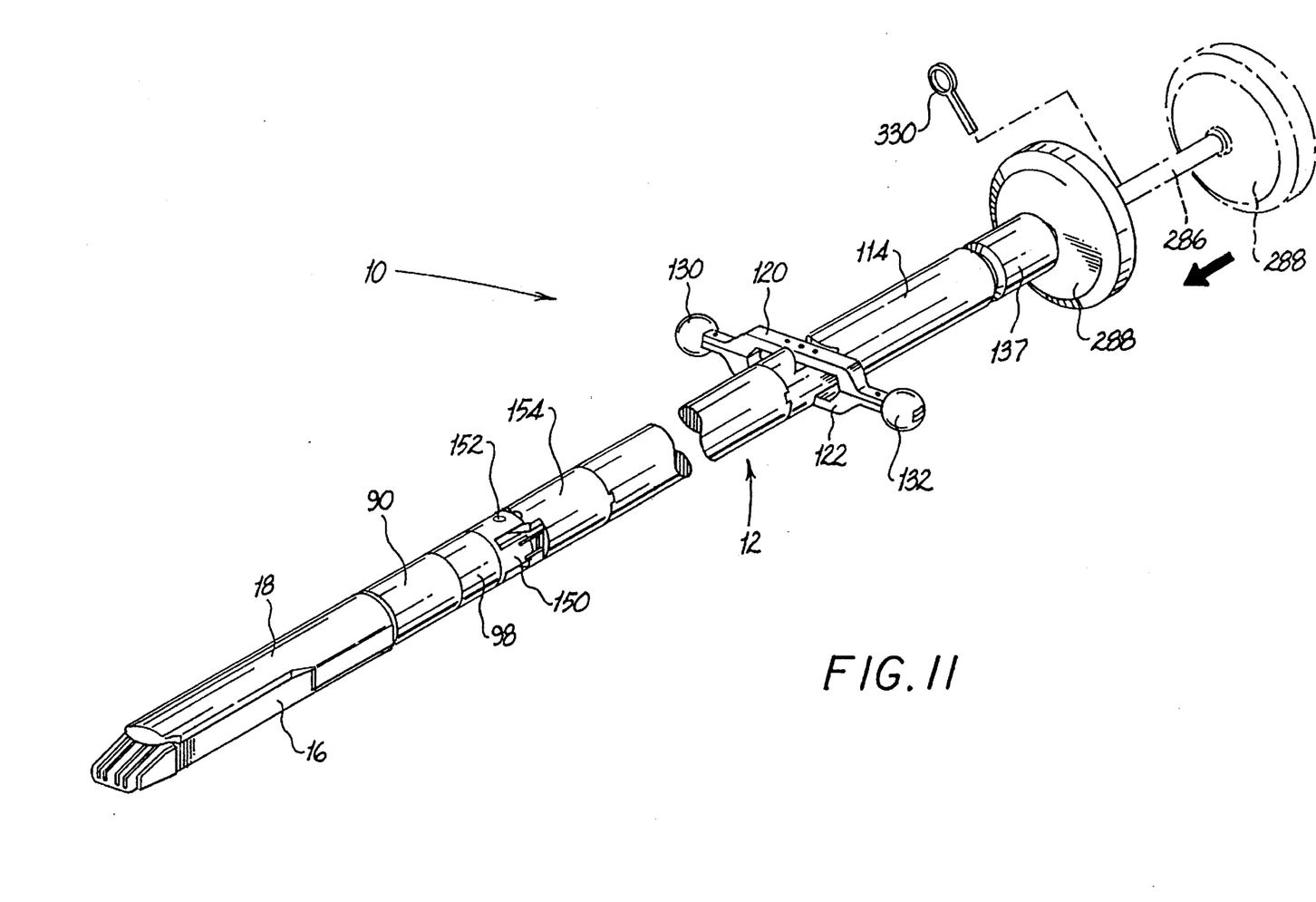
FIG. 11 is a perspective view of the surgical apparatus of FIG. 1, illustrating the actuation of the staple driving mechanism thereof.
Figures 12, 13:
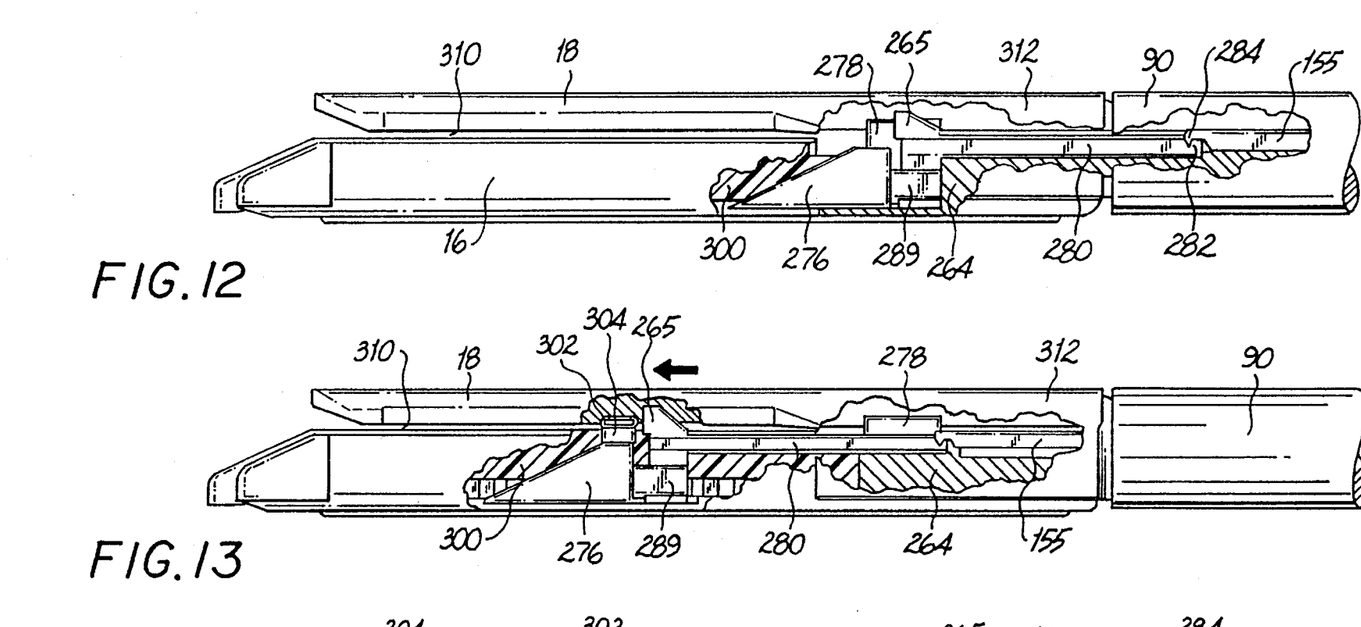
FIG. 12 illustrates the cartridge assembly before the apparatus of FIG. 1 has been fired.
FIG. 13 illustrates the cartridge assembly as the apparatus of FIG. 1 is being fired.
Figure 14:
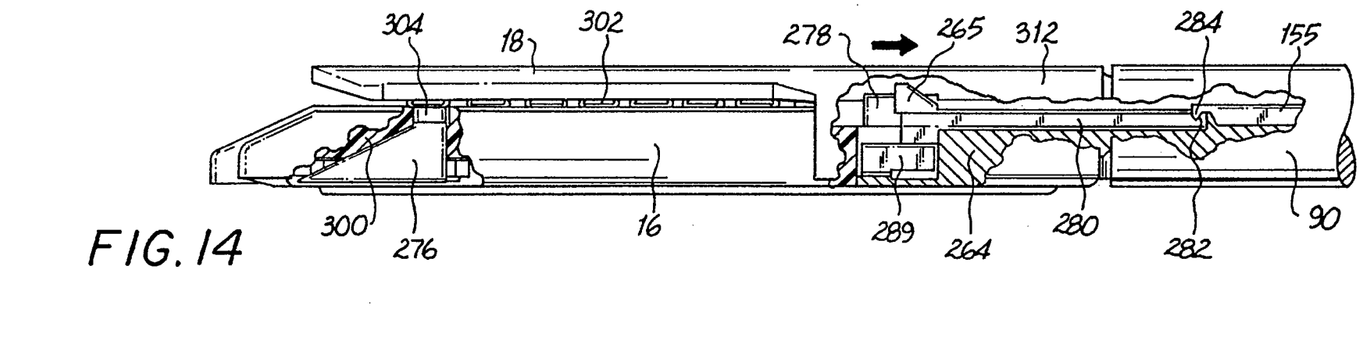
FIG. 14 illustrates the cartridge assembly after the apparatus of FIG. 1 has been fired.

Turning now to FIG. 11, once the body tissue has been engaged in the cartridge assembly, and anvil member 18 has been cammed into a closed position wherein the tissue engaging surface of cartridge housing 16 is in close cooperable alignment with the staple forming surface of anvil member 18, the user may fire the instrument to drive two staggered rows of surgical fasteners as surgical knife 265 simultaneously makes a longitudinal incision between the staple rows. However, prior to firing surgical apparatus 10, the user must remove a safety lock pin 330 engaged in actuator rod 286 adjacent the proximal end of handle clamp 137. While safety lock pin 330 engages, surgical apparatus 10 cannot be fired since actuator link 155 is maintained in a fixed position. Once the lock pin 330 has been removed, the user may drive actuator rod 286 forward, pushing actuator shaft 155 through clamp rod 56, and urging the surgical knife 265 distally from its initial position of FIG. 12. As surgical knife 265 traverses cartridge housing 16, the winged portion 289 thereof drives cam plate 276 forward, consequently driving pusher elements 304 upwardly within their respective cavities 306, to urge staples 302 from the cartridge element 300, as shown in FIG. 13. Once the staples 302 have been ejected from the cartridge 300, the surgical knife 265 is drawn proximally, out of the cartridge housing 16 as actuator link 155 is withdrawn from clamp rod 56, leaving the cam plate 276 in its distal-most position at the distal end of cartridge element 300, as illustrated in FIG. 14. Retraction of the surgical knife 265 into the proximal portion of support bar 278, prevents accidental injury when cartridge assembly 16 is removed from distal joint member 150 so as to be replaced by a loaded cartridge by depressing leaf spring 240.

Although the subject invention has been described with respect to a preferred embodiment, it will be apparent to one skilled in the art that modifications or changes may be made thereto without departing from the spirit or scope of the subject invention as defined by the appended claims.

What is claimed is:

1. Apparatus for driving surgical fasteners comprising:
   a) a body having a proximal portion and an articulating distal portion;
   b) linkage structure extending between said proximal portion and said distal portion of said body and operatively associated with said proximal portion of said body for moving said distal portion relative to a longitudinal axis of said proximal portion;
   c) a cartridge assembly mounted adjacent said articulating distal portion and having a tissue engaging surface thereon;
   d) an anvil member having a fastener forming surface thereon, said anvil member mounted adjacent said cartridge assembly for relative movement between an open position wherein said fastener forming surface is spaced from said tissue engaging surface and a closed position wherein said fastener forming surface is in close cooperative alignment with said tissue engaging surface;
   e) camming means associated with said articulating distal portion for moving said anvil member between said open position and said closed position; and
   f) means for ejecting said surgical fasteners from said cartridge assembly to form against said fastener forming surface of said anvil member.

2. Apparatus as recited in claim 1, wherein said linkage structure for moving said distal portion comprises a linkage assembly including a pair of parallel rod members extending from an articulation link disposed remote from said articulating distal portion.

3. Apparatus as recited in claim 1, wherein said camming means for moving said anvil member between said open position and said closed position includes a tubular collar disposed around at least a portion of said cartridge assembly and said anvil member, said tubular collar having a distal camming surface and being movable between a first position in which said camming surface is located proximal to a camming portion of said anvil member, and a second position in which said camming surface is engaged with said camming portion of said anvil member, said tubular collar cooperating with said anvil member such that when the collar is moved from said first position to said second position said anvil member is urged to said closed position.

4. Apparatus as recited in claim 3, further comprising means for moving said tubular collar between said first position and said second position.

5. Apparatus as recited in claim 4, wherein said means for moving said tubular collar includes an actuator shaft extending from a handle disposed remote from said tubular collar and interconnecting with a pair of flexible pusher bars mounted to said tubular collar in diametrically opposed positions.

6. Apparatus as recited in claim 3, wherein said anvil member is normally biased in said open position.

7. Apparatus as recited in claim 1, wherein said means for ejecting said surgical fasteners from said cartridge assembly comprises an elongated plunger extending from an actuator handle disposed remote from said cartridge assembly to a cam plate in said cartridge assembly adapted and configured for traversing said cartridge assembly for ejecting surgical fasteners therefrom.

8. Apparatus as recited in claim 7, further comprising knife means adapted for longitudinal movement in said cartridge assembly.

9. Apparatus as recited in claim 1, further comprising sealing means associated with said body for inhibiting the egress of gas therethrough.

10. Apparatus for driving surgical fasteners comprising:
   a) a body having a proximal portion and an articulating distal portion;
   b) linkage structure extending between said proximal portion and said distal portion of said body and operatively associated with said body for moving said distal portion relative to a longitudinal axis of said proximal portion;
   c) a cartridge assembly mounted adjacent said articulating distal portion and having a tissue engaging surface thereon;
   d) an anvil member having a fastener forming surface thereon and a camming portion, said anvil member mounted adjacent said cartridge assembly for relative movement between an open position wherein said fastener forming surface is spaced from said tissue engaging surface and a closed position wherein said fastener forming surface is in close cooperative alignment with said tissue engaging surface;
   e) camming means associated with said distal portion for cooperating with said camming portion of said anvil member for moving said anvil member between said open position and said closed position;
   f) means for moving said camming means between a first position corresponding to said anvil member being in an open position and a second position corresponding to said anvil member being in a closed position; and g) means for ejecting said surgical fasteners from said cartridge assembly to form against said fastener forming surface of said anvil member.

11. Apparatus as recited in claim 10, wherein said linkage structure for moving said distal portion comprises a linkage assembly including a pair of parallel rod members extending frown an articulation link disposed remote from said articulating distal portion.

12. Apparatus as recited in claim 10, wherein said camming means for moving said anvil member between said open position and said closed position includes a tubular collar disposed around at least a portion of said cartridge housing and said anvil member, said tubular collar having a distal camming surface and being movable between a first position in which said camming surface is located proximal to the camming portion of said anvil member, and a second position in which said camming surface is engaged with the camming portion of said anvil member.

13. Apparatus as recited in claim 12, wherein said anvil member is normally biased in said open position.

14. Apparatus as recited in claim 10, wherein said means for moving said tubular collar between said first position and said second position includes an actuator shaft extending from a handle disposed remote from said tubular collar and interconnecting with a pair of flexible pusher bars mounted to said tubular collar in diametrically opposed positions.

15. Apparatus as recited in claim 10, wherein said means for ejecting said surgical fasteners from said cartridge assembly comprises an elongated plunger extending from an actuator handle disposed remote from said cartridge assembly to a cam plate in said cartridge assembly adapted and configured for traversing said cartridge assembly for ejecting surgical fasteners.

16. Apparatus as recited in claim 15, further comprising knife means adapted for longitudinal movement in said cartridge assembly.

17. Apparatus as recited in claim 10, further comprising sealing means associated with said body for inhibiting the egress of gas therethrough.

18. Apparatus for driving surgical fasteners comprising:

a) a body having a proximal portion and an articulating distal portion;

b) linkage structure extending between said proximal portion and said distal portion of said body and operatively associated with said body for remotely moving said distal portion relative to a longitudinal axis of said proximal portion;

c) a cartridge assembly mounted adjacent said articulating distal portion and having a tissue engaging surface thereon;

d) an anvil member having a fastener forming surface thereon, said anvil member mounted adjacent said cartridge assembly for relative movement between an open position wherein said fastener forming surface is spaced from said tissue engaging surface and a closed position wherein said fastener forming surface is in close cooperative alignment with said tissue engaging surface;

e) camming means associated with said distal portion for moving said anvil member between said open position and said closed position;

f) means positioned adjacent a proximal end of said body for remotely moving said camming means between a first position corresponding to said anvil member being in an open position and a second position corresponding to said anvil member being in a closed position; and g) means positioned adjacent a proximal end of said body for remotely ejecting said surgical fasteners from said cartridge assembly to form against said fastener forming surface of said anvil member.

19. Apparatus as recited in claim 18, wherein said linkage structure for moving said distal portion comprises a linkage assembly including a pair of parallel rod members extending from an articulation link disposed remote from said articulating distal portion.

20. Apparatus as recited in claim 18, wherein said camming means for moving said anvil member between said open position and said closed position includes a tubular collar disposed around at least a portion of said cartridge assembly and said anvil member, said tubular collar having a distal camming surface and being movable between a first position in which said camming surface is located proximal to a camming portion of said anvil member, and a second position in which said camming surface is engaged with the camming portion of said anvil member.

21. Apparatus as recited in claim 20, wherein said means for moving said tubular collar between said first position and said second position includes an actuator shaft extending from a handle disposed remote from said tubular collar and interconnecting with a pair of flexible pusher bars mounted to said tubular collar in diametrically opposed positions.

22. Apparatus as recited in claim 20, wherein said anvil member is normally biased in said open position.

23. Apparatus as recited in claim 18, wherein said means for ejecting said surgical fasteners from said cartridge assembly comprises an elongated plunger extending from an actuator handle disposed remote from said cartridge assembly to a cam plate in said cartridge assembly adapted and configured for traversing said cartridge assembly for ejecting surgical fasteners.

24. Apparatus as recited in claim 23, wherein a surgical knife is associated with said cam plate and is adapted for longitudinal movement therewith.

25. Apparatus as recited in claim 18, further comprising sealing means associated with said body for inhibiting the egress of gas therethrough.

26. Apparatus for driving surgical fasteners comprising:

a) a body having a proximal portion and an articulating distal portion;

b) a linkage assembly interconnecting said proximal portion and said distal portion of said body and operatively associated with said proximal portion of said body for remotely moving said distal portion relative to a longitudinal axis of said proximal portion;

c) a cartridge assembly mounted adjacent said articulating distal portion and having a tissue engaging surface thereon;

d) an anvil member having a fastener forming surface thereon, said anvil member mounted adjacent said cartridge assembly for relative movement between an open position wherein said fastener forming surface is spaced from said tissue engaging surface and a closed position wherein said fastener forming surface is in close cooperative alignment with said tissue engaging surface;

e) a camming assembly associated with said articulating distal portion for moving said anvil member between said open position and said closed position; and f) an actuation assembly for ejecting said surgical fasteners from said cartridge assembly to form against said fastener forming surface of said anvil member.

27. Apparatus as recited in claim 26, wherein said linkage assembly comprises a pair of parallel rod members extending from an articulation link disposed remote from said articulating distal portion.

28. Apparatus as recited in claim 26, wherein said camming assembly for moving said anvil member between said open position and said closed position includes a tubular collar disposed around at least a portion of said cartridge assembly and said anvil member, said tubular collar having a distal camming surface and being movable between a first position in which said camming surface is located proximal to a camming portion of said anvil member, and a second position in which said camming surface is engaged with said camming portion of said anvil member, said tubular collar cooperating with said anvil member such that when the collar is moved from said first position to said second position said anvil member is urged to said closed position.

29. Apparatus as recited in claim 28, further comprising an actuator moving said tubular collar between said first position and said second position.

30. Apparatus as recited in claim 26, wherein said actuation assembly includes an elongated plunger extending from an actuator handle disposed remote from said cartridge assembly to a cam plate in said cartridge assembly, said cam plate being movable through said cartridge assembly for contacting a plurality of pusher elements to eject surgical fasteners therefrom.

* * * * *